United States Patent [19]

Zenzon et al.

[11] Patent Number: 5,538,512

[45] Date of Patent: *Jul. 23, 1996

[54] LUBRICIOUS FLOW DIRECTED CATHETER

[76] Inventors: Wendy J. Zenzon, 39541 Gallaudet Dr. #1008, Fremont, Calif. 94538; Uriel H. Chee, 127 Dolton Ave., San Carlos, Calif. 94030; Joseph C. Eder, 364 Marich Way, Los Altos, Calif. 94022; Robert Hergenrother, 171 Blaisdell Way, Fremont, Calif. 94536

[ * ] Notice: The term of this patent shall not extend beyond the expiration date of Pat. No. 5,336,205.

[21] Appl. No.: 272,209

[22] Filed: Jul. 8, 1994

Related U.S. Application Data

[63] Continuation-in-part of Ser. No. 23,805, Feb. 25, 1993, Pat. No. 5,336,205.

[51] Int. Cl.⁶ .................................................... A61M 25/00
[52] U.S. Cl. ............................ 604/280; 604/264; 604/93; 604/53
[58] Field of Search ............................... 604/96, 53, 265, 604/280–282, 93, 95, 264; 128/658

[56]          References Cited

U.S. PATENT DOCUMENTS

| | | |
|---|---|---|
| 2,857,915 | 10/1958 | Sheridan . |
| 3,228,894 | 1/1966 | Jeckel . |
| 3,370,587 | 2/1968 | Vizcarra . |
| 3,566,874 | 3/1971 | Shepherd et al. . |
| 3,608,555 | 9/1971 | Greyson . |
| 3,746,003 | 7/1973 | Blake et al. . |
| 3,749,134 | 7/1973 | Slinguff et al. . |
| 3,866,599 | 2/1975 | Johnson . |
| 3,995,623 | 12/1976 | Blake et al. . |
| 4,024,873 | 5/1977 | Antoshkiw et al. . |
| 4,169,464 | 10/1979 | Obrez . |
| 4,276,874 | 7/1981 | Wolvek et al. . |
| 4,329,993 | 5/1982 | Lieber et al. . |
| 4,385,635 | 5/1983 | Ruiz . |
| 4,596,563 | 6/1986 | Pande . |
| 4,610,690 | 9/1986 | Tiffany ......................................... 623/8 |
| 4,636,346 | 1/1987 | Gold et al. . |
| 4,694,838 | 9/1987 | Wijayarthna et al. . |
| 4,696,304 | 9/1987 | Chin . |
| 4,721,115 | 1/1988 | Owens . |
| 4,739,768 | 4/1988 | Engelson . |
| 4,747,840 | 5/1988 | Ladika et al. . |
| 4,758,221 | 7/1988 | Jureidini . |
| 4,762,130 | 8/1988 | Fogarty et al. . |
| 4,840,622 | 6/1989 | Hardy . |
| 4,883,058 | 11/1989 | Ruiz . |
| 4,884,579 | 12/1989 | Engelson . |
| 4,898,591 | 2/1990 | Jang et al. . |
| 4,963,306 | 10/1990 | Weldon . |

(List continued on next page.)

FOREIGN PATENT DOCUMENTS

| | | |
|---|---|---|
| 0362497 | 4/1990 | European Pat. Off. . |
| 0517075 | 12/1992 | European Pat. Off. . |
| WO92/15356 | 9/1992 | WIPO . |
| WO93/02733 | 2/1993 | WIPO . |

OTHER PUBLICATIONS

Dion, J. E., et al., "Progressive suppleness pursil catheter: A new tool for superselective angiography and embolization" *AJNR* (Sep./Oct. 1989) 10: 1068–1070.

Target Therapeutics Product Brochure entitled "Zephyr® flow–assisted infusion catheter" (1991) Target Therapeutics, 130 Rio Robles, San Jose, CA 95134, 4 pages total.

*Primary Examiner*—Randall L. Green
*Assistant Examiner*—Perry E. Van Over
*Attorney, Agent, or Firm*—Morrison & Foerster

[57]          ABSTRACT

This invention relates to infusion catheters that are used in cardiovascular and endovascular procedures to deliver diagnostic, therapeutic or vasoocclusive agents to a target site (the target site being accessible by a tortuous path through the vasculature). In particular, the invention relates to flow-directed catheters which have been coated on their interior or exterior surfaces with a cross-linkable lubricious polymer and to the method of making those catheters. The invention also relates to the process of using the infusion catheter.

23 Claims, 3 Drawing Sheets

U.S. PATENT DOCUMENTS

| | | |
|---|---|---|
| 4,994,069 | 2/1991 | Ritchart et al. . |
| 5,016,640 | 5/1991 | Ruiz . |
| 5,037,404 | 8/1991 | Gold et al. . |
| 5,069,673 | 12/1991 | Shwab . |
| 5,171,232 | 12/1992 | Castillo et al. . |
| 5,234,416 | 8/1993 | Macaulay et al. . |
| 5,254,107 | 10/1993 | Soltesz . |
| 5,322,509 | 6/1994 | Rickerd . |
| 5,336,205 | 8/1994 | Zenzen et al. ............... 604/280 |
| 5,342,386 | 8/1994 | Trotta . |
| 5,348,545 | 9/1994 | Shani et al. . |
| 5,397,306 | 3/1995 | Nobuyoshi et al. . |

LUBRICIOUS FLOW DIRECTED CATHETER

RELATED APPLICATIONS

This is a continuation-in-part of U.S. patent application Ser. No. 08/023,805, entitled "FLOW DIRECTED CATHETER", by Zenzen et al., filed Feb. 25, 1993, now U.S. Pat. No. 5,336,205.

FIELD OF THE INVENTION

The present invention is in the general field of surgical instruments. Specifically, it relates to infusion catheters that are used in cardiovascular and endovascular procedures to deliver diagnostic, therapeutic or vasoocclusive agents to a target site (the target site being accessible by a tortuous path through the vasculature). In particular, the invention relates to surgical devices which have been coated on their interior or exterior surfaces with a cross-linkable lubricious polymer and to the method of making those catheters. The invention also relates to the process of using the infusion catheter.

BACKGROUND

Catheters are being used increasingly as a means for delivering diagnostic or therapeutic agents to internal target sites that can be accessed through the circulatory system. There are a number of general approaches for placing catheters within vessels in the body that are difficult to access. In one such technique, a torqueable guidewire is alternately rotated and advanced to the target site. With the wire in place, the catheter is then advanced along the wire until the distal end of the catheter is positioned at the target site. An example of this technique is described in U.S. Pat. No. 4,884,579. A major drawback to this approach is the time-consuming nature of rotating and advancing the guidewire and catheter through the vasculature.

A second technique for advancing a catheter to a target site is to employ a highly flexible catheter having an inflatable, but pre-punctured balloon at its distal end. In use, the balloon is partially inflated, and carried by blood flow into the target site. During placement, the balloon is continually inflated to replenish fluid leaking from the balloon. This technique, too, has major drawbacks including the fact that the catheter material is so floppy that it cannot be pushed without buckling, and instead must be advanced using injected fluid to inflate the balloon in order to propel the catheter to the target site. Additionally, there is a significant risk of rupture of a vessel by a balloon that has been overinflated.

In order to address some of the above described problems, another approach has involved the use of flexible catheters that can be directed to a target site as a result of the blood flowing to that site. In 1991, Target Therapeutics released a product known as the "ZEPHYR" flow-assisted infusion catheter. The product was designed to be introduced into the vasculature through a guiding catheter and then allowed to be directed by the blood flow to a target site. The catheter comprised segments of different materials, a proximal segment made of nylon, and middle and distal segments made of a block copolymer of polyamide. The product proved to be unsuccessful in achieving its desired function as it was not flexible enough to navigate the tortuous vessel pathway and not strong enough to withstand the required injection pressure.

The present invention is an infusion catheter assembly useful for the delivery of diagnostic, therapeutic or vasoocclusive agents to remote portions of the vascular system, particularly to diagnose or treat arteriovenous malformations (AVMs). The invention also includes a process for placing the infusion catheter at the target site and a process for delivering a diagnostic, therapeutic or vasoocclusive agent to the target site.

SUMMARY OF THE INVENTION

This invention is an infusion catheter for placement within a tortuous, small vessel pathway and a method for delivery of an agent to a target site. The infusion catheter is directed to the target site by means of the flow of blood to that site. The infusion catheter has an elongate tubular body having proximal and distal ends and a lumen extending between the ends through which the diagnostic, therapeutic, or vasoocclusive agent can be delivered. One variation of this invention is a catheter having a coated inside diameter or outer surface. The coating is very slippery and quite durable.

The elongate tubular body is preferably formed of a relatively stiff tapered proximal segment, a relatively flexible and strong distal segment, and a transition section between the proximal and distal segments that is less flexible than the distal segment but more flexible than the proximal segment. The distal segment has a burst pressure of at least about 195 psi and is made of a material that will show a force of about $1 \times 10^{-4}$ or less when ten centimeters of the material is deflected 10° from horizontal.

A further aspect of the invention is a method for accessing a target site. A guiding catheter is inserted into the vasculature. An infusion catheter is then inserted into the guiding catheter. A stylet may optionally be used to straighten the soft, flexible distal end of the infusion catheter for easy insertion into the guiding catheter. If the stylet is used, it is removed once the infusion catheter is inside the guiding catheter. The infusion catheter is then pushed out of the guiding catheter into the vasculature. The blood flow in the vasculature directs the infusion catheter to the target site.

Yet another aspect of the invention is a method for delivering a diagnostic, therapeutic, or vasoocclusive agent to a target site. The infusion catheter is inserted into the vasculature by means of a guiding catheter. The infusion catheter is positioned at the target site as a result of the blood flow to the target site. The diagnostic, therapeutic or vasoocclusive agent is then injected through the catheter lumen and infused into the target site.

The exterior or interior of the catheter bodies may be coated with hydrophilic polymeric materials by a method involving application of the polymer from a dilute polymer or oligomer solution desirably followed by simultaneous solvent removal and curing of the applied precursor. Curing of the catheter interior takes place by use of a quartz or glass fiber dip-leg placed within the catheter lumen. The dip-leg fiber radiates UV radiation to the interior of the catheter and, in some instances, to the exterior of the catheter for curing the polymeric material found there. Multiple coatings of the polymeric material may be useful.

DETAILED DESCRIPTION OF THE INVENTION

This invention is a catheter having an exterior or interior surface which has been coated with a lubricious polymer and which coating has been cross-linked in situ and covalently bonded to the catheter using irradiation.

Figure 1:
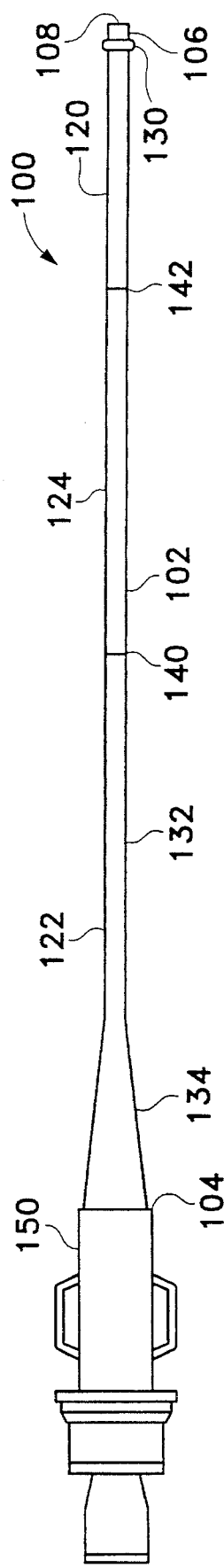
FIG. 1 is a diagram that shows an infusion catheter constructed according to a preferred embodiment of the present invention.

FIG. 1 shows an infusion catheter 100 constructed according to a preferred embodiment of the invention. The catheter 100 has an elongate tubular body 102 with proximal 104 and distal 106 ends and an inner lumen 108 extending between the ends. The elongate tubular body 102 is comprised of three segments; a relatively flexible and strong distal segment 120, a relatively stiff tapered proximal segment 122 and a transition section 124 between the proximal and distal segments that is less flexible than the distal segment 120 but more flexible than the proximal segment 122.

The elongate tubular body 102 has a relatively flexible and strong distal segment 120 such that the catheter can easily navigate a tortuous vessel pathway. By relatively flexible is meant that a force of about $1 \times 10^{-4}$ pounds corresponds to a deflection of the material that is 10° from horizontal, or only about $5 \times 10^{-4}$ pounds of force to deflect the material about 80° from horizontal. By relatively strong is meant that the material has a burst pressure of greater than 195 psi, more preferably the burst pressure is between about 195 and 220 psi.

The flexible distal segment 120 has an open end which allows for the infusion of diagnostic, therapeutic or vasoocclusive agents into the target site. The flexible distal segment 120 is made of a polymer that is springy and biologically compatible such as polyurethane, a block copolymer of polyamide, polyvinyl chloride, or silicone or blends of the above. The flexible distal segment 120 carries one or more radiopaque bands 130 or may be doped with a radiopaque material such as barium sulfate, bismuth trioxide, bismuth subcarbonate, tungsten, tantalum or the like so that the location of the distal region of the catheter within the vessel may be visualized radiographically. The distal segment 120 makes up between about 5 and 25% of the total length of the tubular member and is between about 5 and 40 cm long, preferably between about 10 and 20 cm long. The inner diameter of the distal segment 120 is between about 0.25 and 0.50 mm, more preferably between about 0.25 and 0.35 mm. The outer diameter of the distal segment is between about 0.50 and 0.80 mm, more preferably between about 0.60 and 0.70 mm. The wall thickness of the distal segment 120 is between about 0.1 and 0.3 mm.

The proximal segment 122 of the elongate tubular body 102 is relatively stiff such that it can be easily pushed thus eliminating the need for guidewire support. The proximal segment 122 is made of a polymeric or metallic material that is relatively stiff and biologically compatible such as nylon, polyvinyl chloride, polyethylene terephthalate or other polyester elastomers or a braided shaft (a polymer outer core with a metallic mesh inner core). The proximal segment 122 comprises a tapered proximal section 134 for attachment to the proximal end fitting 150 and a distal section 132. The proximal section 134 of proximal segment 122 makes up between about 60% and 80% of the total length of the tubular member 102 and is between about 90 and 130 cm long, preferably between about 100 and 120 cm long. The largest inner diameter of the proximal section 134 (at the proximal end 104 of the tubular member 102) is between about 0.40 and 0.60 mm, more preferably between about 0.45 and 0.55 mm. The outer diameter of the proximal section 134 at the proximal end 104 of the tubular member 102 is between about 0.8 and 1.2 mm. The wall thickness of the proximal section 134 of proximal segment 122 is between about 0.1 and 0.4 mm, more preferably between about 0.2 and 0.3 mm.

The distal section 132 of proximal segment 122 makes up between 10 and 20% of the total length of the tubular body 102 and is between about 20 and 40 cm long, preferably between about 20 and 30 cm long. The inner diameter of the distal section 132 of proximal segment 122 is between about 0.20 and 0.50 mm, more preferably between about 0.25 and 0.35 mm. The outer diameter of the distal section 132 of proximal segment 122 is between about 0.60 and 0.90 mm, more preferably between about 0.60 and 0.70 mm. The wall thickness of the distal section 134 of proximal segment 122 is between about 0.1 and 0.3 mm.

The transition section 124 of the elongate tubular body 102 is less stiff than the proximal segment 122 but more stiff than the distal segment 120. A suitable material that is biologically compatible is a polymer such as polyurethane, a block copolymer of polyamide, polyvinyl chloride or silicone with greater durometer (i.e. that is stiffer) than the flexible distal segment 120. The transition section 124 may be radiopaque and thus observable in the event that the catheter becomes lodged in a particular portion of the vasculature or buckles, and as such the polymeric material is doped with a radiopaque material such as barium sulfate, bismuth subcarbonate, bismuth trioxide, tungsten, tantalum or the like. The transition section 124 makes up between about 10 and 20% of the total length of the tubular member 102 and is between about 20 and 40 cm long, preferably between about 25 and 35 cm long. The transition section 124 may be of constant diameter or may be tapered. The inner diameter of the transition section 124 is between about 0.20 and 0.50 mm, more preferably between about 0.20 and 0.35 mm. The outer diameter of the transition section 124 is between about 0.50 and 0.90 mm, more preferably between about 0.60 and 0.70 mm. The wall thickness of the transition section 124 is between about 0.1 and 0.3 mm.

The proximal segment 122, transition section 124 and distal segment 120 are joined at junctions 140 and 142, respectively. The junctions are formed by flaring, overlapping and heat fusing the materials of the proximal segment 122 and transition section 124 and the transition section 124 and distal segment 120. The distal segment 120, transition section 124 and distal section 132 of proximal segment 122 may all have approximately the same outside diameter or the transition section 124 and the distal section 132 of the proximal segment 122 may be tapered.

A standard proximal end fitting 150 is attached to the proximal section 134 of the proximal segment 122 by heat fusion with reinforcing tubing.

Figure 2:
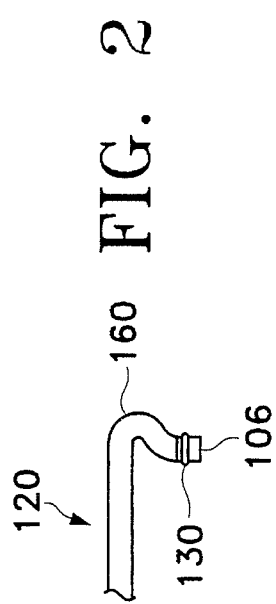
FIG. 2 is a diagram that shows the distal end on one embodiment of the infusion catheter of the present invention wherein the distal end is formed in an "S" shaped configuration.

FIG. 2 shows one embodiment of the distal segment 120 of the catheter wherein the tip 160 of the catheter is shaped with steam such that the distal end 106 points to the wall of the vessel rather that straight into the path of blood flow for ease of manipulation through the tortuous vessel pathway. The particular embodiment shown is an "S" shape, but the tip may be any shape that allows for access to the particular vasculature being treated. In this way, if the catheter becomes lodged against the vessel wall, the infusion of liquid through the catheter propels the distal end 106 of the catheter away from the vessel wall. As the stiff proximal segment 122 is pushed, the distal segment 120 will be carried by the blood flood to the target site.

The catheter described above is useful in delivering diagnostic, therapeutic, or vasoocclusive agents to deep tissue.

Figure 3:
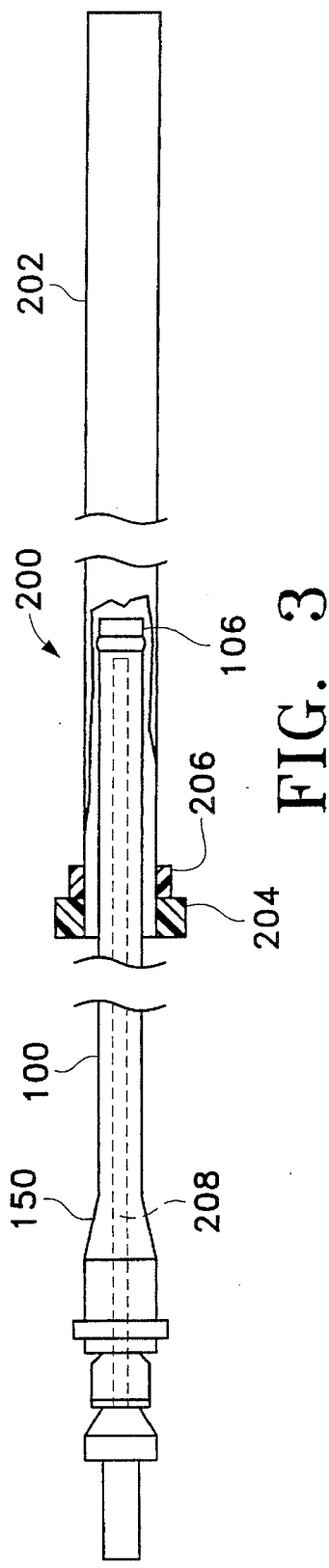
FIG. 3 is a diagram that shows an infusion catheter, stylet and guiding catheter assembly.

FIG. 3 shows a catheter assembly 200 for placing the infusion catheter 100 at the target site. An appropriate guiding catheter 202 is inserted into the vasculature using standard placement techniques. A rotating hemostatic valve 204 is connected to the guiding catheter luer adapter 206. The guiding catheter 202 is continuously flushed with saline. The thumb-screw of the valve 204 is opened and the infusion catheter 100 is inserted through the rotating hemostatic valve 204. Optionally, as shown in FIG. 3, a Teflon-coated stainless steel stylet 208 is first inserted into the infusion catheter 100 in order to prevent kinking of the infusion catheter 100 within the valve 204. The distal end 106 of the infusion catheter 100 is advanced proximal to the tip of the guiding catheter 202. The stylet 208 is then removed from the infusion catheter 100. Once the stylet 208 is removed, the infusion catheter 100 is pushed out of the guiding catheter 202. The infusion catheter 100 is gently guided by the flow of blood in the vasculature to the target site. Optionally, gentle pushing and pulling and injection of saline or contrast medium through the catheter lumen 108 may aid in the placement of the catheter at the target site.

Coatings

Particularly suitable as coatings in the catheter assembly of this invention are polymers or oligomers of monomers selected from ethylene oxide and its higher homologs including up to 6 carbon atoms; 2-vinyl pyridine; N-vinylpyrrolidone; polyethylene glycol acrylates such as monoalkoxy polyethylene glycol mono(meth) acrylates, including mono-methoxy triethylene glycol mono (meth) acrylate, mono-methoxy tetraethylene glycol mono (meth) acrylate, polyethylene glycol mono (meth) acrylate; other hydrophilic acrylates such as 2-hydroxyethylmethacrylate, glycerylmethacrylate; acrylic acid and its salts; acrylamide and acrylonitrile; acrylamidomethylpropane sulfonic acid and its salts, cellulose, cellulose derivatives such as methyl cellulose ethyl cellulose, carboxymethyl cellulose, cyanoethyl cellulose, cellulose acetate, polysaccharides such as amylose, pectin, amylopectin, alginic acid, and cross-linked heparin; maleic anhydride; aldehydes; etc. These monomers may be formed into homopolymers or block or random copolymers. The use of oligomers of these monomers in coating the catheter for further polymerization is also an alternative. Preferred monomers include ethylene oxide; 2-vinyl pyridine; N-vinylpyrrolidone and acrylic acid and its salts; acrylamide and acrylonitrile each polymerized (with or without substantial crosslinking) into homopolymers, or into random or block copolymers.

Additionally, hydrophobic monomers may be included in the polymeric coating material in an amount up to about 30% by weight of the resulting copolymer so long as the hydrophilic nature of the resulting copolymer is not substantially compromised. Suitable monomers include ethylene, propylene, styrene, styrene derivatives, alkylmethacrylates, vinylchloride, vinylidenechloride, methacrylonitrile, and vinyl acetate. Preferred, because of their propensity for ease of linkage to the typical polymeric catheter substrates, are ethylene, propylene, styrene, and styrene derivatives.

Polymers or oligomers applied using the procedure described below are activated or functionalized with photoactive or radiation-active groups to permit reaction of the polymers or oligomers with the underlying polymeric surface. Suitable activation groups include benzophenone, thioxanthone, and the like; acetophenone and its derivatives specified as:

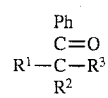

where $R^1$ is H, $R^2$ is OH, $R^3$ is Ph; or $R^1$ is H, $R^2$ is an alkoxy group including $—OCH_3$, $—OC_2H_3$, $R^3$ is Ph; or $R^1=R^2=$an alkoxy group, $R^3$ is Ph; or $R^1=R^2=$an alkoxy group, $R^3$ is H; or $R^1=R^2=Cl$, $R^3$ is H or Cl.

Other known activators are suitable.

The polymeric coating may then be linked with the substrate using known and appropriate techniques selected on the basis of the chosen activators preferably by ultraviolet light but also by heat or ionizing radiation. Crosslinking or curing with the listed polymers or oligomers may be accomplished by use of peroxides or azo compounds such as acetyl peroxide, cumyl peroxide, propionyl peroxide, benzoyl peroxide, or the like. A polyfunctional monomer such as divinylbenzene, ethylene glycol dimethacrylate, trimethylolpropane, pentaerythritol di- (or tri- or tetra-) methacrylate, diethylene glycol, or polyethylene glycol dimethacrylate, and similar multifunctional monomers capable of linking the polymers and oligomers discussed above is also appropriate for this invention.

The polymeric coating may be applied to the exterior of the catheter body or other polymeric substrate by any of a variety of methods, e.g., by spraying a solution or suspension of the polymers or of oligomers of the monomers onto the catheter or by dipping the catheter into the solution or suspension (after sealing the open ends, if so desired). Initiators may be included in the solution or applied in a separate step. The catheter may be sequentially or simultaneously dried to remove solvent after application of the polymer or oligomer to the exterior of the polymeric body and crosslinked.

Procedure for Inside Diameter Coating

The polymeric coating may be applied to the interior of the catheter by use of pressure forcing the precursor fluid through that interior. Because of the difficulty of achieving a reasonably smooth and even layer within that interior, it is preferred that the polymer precursor solution used for the catheter interior be cured by UV or by ionizing radiation. This is so because the polymer precursor solution should be physically stable when crosslinked. In some instances, this would mean that the solvent has been substantially removed from the layer coating the interior of the catheter. In other instances, a fluid coating may be present on the interior, but it typically must have had the majority of the solvent removed to allow sufficient concentration of the photoactive groups to mandate the binding of the precursor to the inner catheter lumen. Thin solutions are very, very difficult to polymerize. In the latter case, if a fiber dip-leg is used to activate or cure the photoactive groups and cure the coating, the resulting coating may not be completely uniform, but nevertheless is suitable to enhance the overall slipperiness of the catheter interior. If a fluid coating is used—one that remains liquid (albeit, a concentrated one) during the crosslinking step—ionizing radiation may be used to polymerize the precursor solution since the radiation source does not disturb the coating.

The solution or suspension should be quite dilute since only a very thin layer of polymer is to be applied either to the interior or to the exterior of the catheter. We have found that an amount of oligomer or polymer in a solvent of between 0.25% and 5.0% (wt), preferred is 0.5 to 2.0% (wt), is excellent for thin and complete coverage of the resulting polymer. Preferred solvents for this procedure when using the preferred polymers and procedure are water, low molecular weight alcohols, especially methanol, propanol, isopropanol, ethanol, and their mixtures and ethers. Other water miscible solvents, e.g., tetrahydrofuran, methylene dichloride, methylethylketone, dimethylacetate, ethyl acetate, dimethyl acetamide, etc., are suitable for the listed polymers and must be chosen according to the characteristics of the polymer; they should be polar because of the hydrophilic nature of the polymers and oligomers but, because of the reactivity of the terminal groups of those materials, known quenching effects caused by oxygen, hydroxyl groups, and the like must be recognized by the user of this process when choosing polymers and solvent systems.

Particularly preferred as a coatings for the catheter bodies discussed below are physical mixtures of homo-oligomers of at least one of polyethylene oxide; poly 2-vinyl pyridine; polyvinylpyrrolidone, polyacrylic acid, polyacrylamide, and polyacrylonitrile.

Exterior Coating

When applying a polymeric coating to the exterior of the catheter, the catheter bodies or substrates are preferably sprayed or dipped, dried, and irradiated to produce a polymerized and cured and bonded polymeric skin of the noted monomers or oligomers. The exterior lubricious hydrophilic coating is preferably produced using generally sequential solvent removal and crosslinking operations. The coating is applied at a rate allowing "sheeting" of the solution, e.g., formation of a visibly smooth layer without "runs". In a dipping operation for most polymeric substrates noted below, the optimum coating rates are found at a linear removal rate between 0.25 and 2.0 inches/sec, preferably 0.5 and 1.0 inches/sec.

The solvent evaporation operations may be conducted using a heating chamber suitable for maintaining the surface at a temperature between 25° C. and the glass transition temperature ($T_g$) of the underlying substrate. Preferred temperatures are 50° C. to 125° C. Most preferred for the noted and preferred solvent systems is the range of 75° to 110° C.

Ultraviolet light sources may be used to crosslink the polymer precursors onto the substrate polymeric device. Movement through an irradiation chamber having an ultraviolet light source at 90–375 nm (preferably 300–350 nm) having an irradiation density of 50–1200 mW/cm$^2$, preferably 50–300 mW/cm$^2$, most preferably 150–250 mW/cm$^2$ for a period of three to seven seconds is desired. Passage of a catheter through the chamber at a rate of 0.25 to 2.0 inches/second (0.5 to 1.0 inches/second) in a chamber having three to nine inches length is suitable. When using ionizing radiation, a radiation density of 1 to 100 kRads/cm$^2$ (preferably 20 to 50 kRads/cm$^2$) may be applied to the solution or suspension on the polymeric substrate.

In sum, the process preferably involves the substantive steps of creating a coating of substantial uniformity, drying, and then curing the coating using ultraviolet radiation to produce a coating which is covalently bonded to the substrate.

Exceptional durability of the resulting coating is produced by repetition of the dipping/solvent removal/irradiation steps up to five times. Preferred are two to four repetitions.

Interior Coating

As was the case with applying the polymer precursor to the exterior of the catheter, the solution or suspension of the polymer precursor should be quite dilute. The amount of oligomer or polymer in a solvent may desirably be between 0.10% and 5.0% (wt), preferred is 0.10% to 2.5% (wt) to assure coverage of the interior surface of the catheter. A small amount of a flow additive is also desirable. It must be remembered that the interior diameter of many catheters is perhaps as small as 0.008 inches.

Solvents suitable for this operation are the same as those listed for exterior coating although there is a preference for low molecular weight solvents to lower the overall viscosity of the precursor solution.

Similarly, the polymer precursors listed for use as exterior catheters are also suitable for interior coating.

As was noted above, the coating is preferably applied using a pressurized source to pass the precursor solution through the catheter. Once the catheter is filled. The solution is then expressed to allow the solution to coat the interior but not to form plugs or the like.

Heated air (e.g., at 250°–350° F.) may be introduced into the region of the catheter perhaps with added direct heat, to remove the solvent, and leave a thin coat behind. If a uniform coating is necessary, this step must be carried out at a proper rate to form that uniform coating prior to the irradiation step.

A fused silica (glass or quartz) fiber dip-leg coupled to a UV source is then passed through the catheter lumen at a rate appropriate for crosslinking the polymer. The dip-leg fiber may be coupled to a UV source such as a short-arc mercury lamp or laser. The dip-leg is configured so that the major portion of the UV passes through the tip onto the interior of the catheter lumen. Reflective fibers are excellent for this service.

The dip-leg fiber is moved at a rate proportional to the cross-sectional ID area. For instance, for a catheter having a 0.047" ID, a 1000 watt short arc mercury lamp joined to a fused quartz fiber, the rate would be about 17"/minute.

The steps of coating, dying, and cross-linking may be repeated for two or more iterations.

Figure 4:
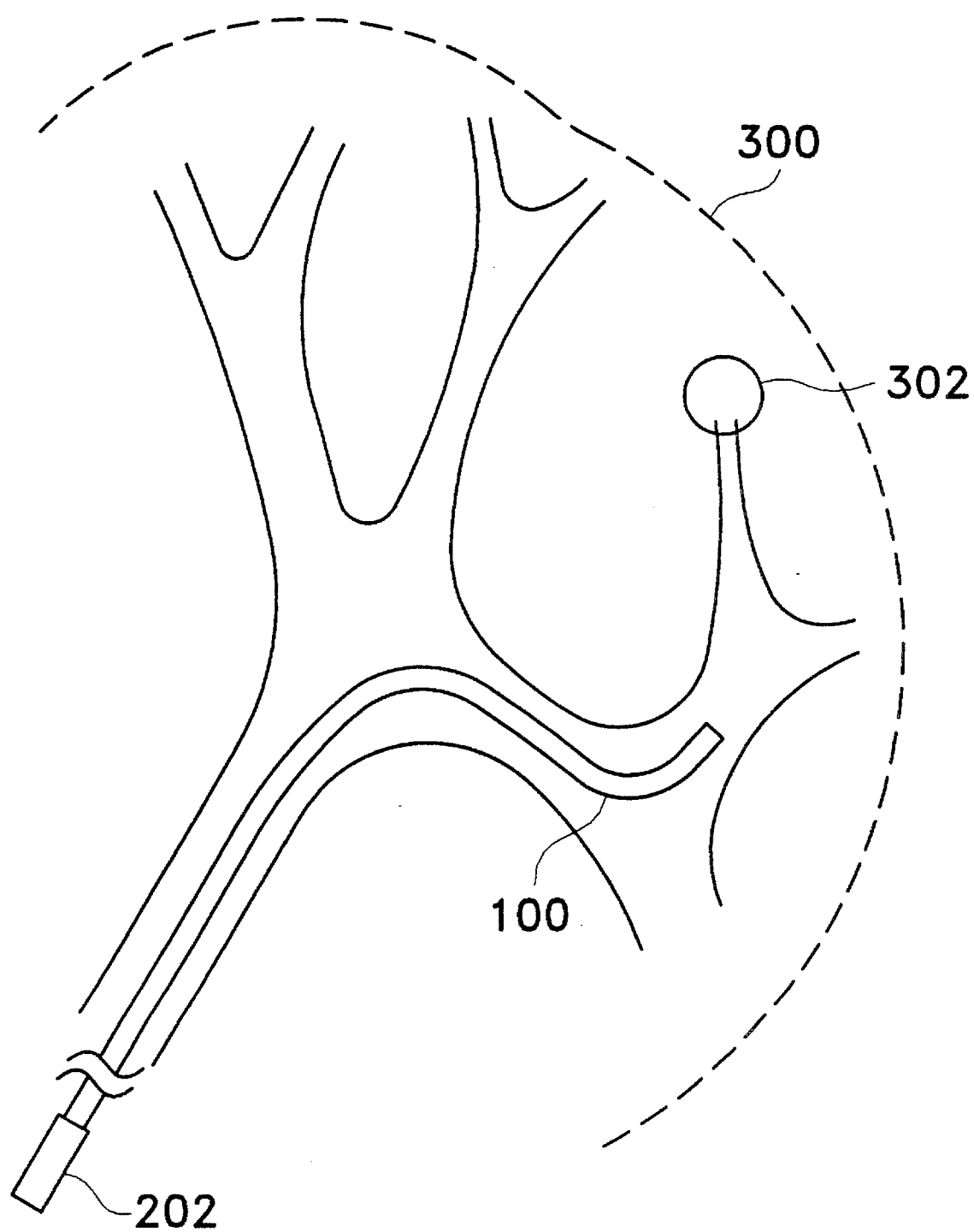
FIG. 4 is an illustration of a portion of a tortuous path in a soft tissue, and the method of guiding the infusion catheter along this path.

FIG. 4 shows the method of inserting the infusion catheter into a tissue region which is reached by a tortuous path. The figure shows a region of soft tissue 300, such as in the region of the brain, containing a target site 302. Initially the guiding catheter, indicated at 202 is fed from a vascular access region. The infusion catheter 100 is inserted into the guiding catheter 202 and then pushed out of the end of the guiding catheter. Blood flow in the vessel then directs the infusion catheter 100 to the target site 302.

Once the infusion catheter is placed at the target site, a syringe may be connected to the proximal end fitting 150 and the diagnostic, therapeutic or vasoocclusive agent may be infused through the catheter lumen 108 and into the target site. The injected agent may include radiopaque agents for viewing blood vessel anatomy and blood flow characteristics in the target region, vasoocclusive agents which can be used to produce small-artery vasoocclusion in the tissue region supplied by the target vessel, and pharmacological agents, such as anti-tumor drugs or sclerosing agents such as alcohols, which are effective against identified disease states at the target site. Vasoocclusive agents useful in the treatment of arteriovenous malformations include polymers that are activated in the presence of polar solvents such as water and include materials such as n-butylcyanoacrylate. Other types of vasoocclusive agents useful in the treatment of arteriovenous malformations include polymer solutions that coagulate by diffusion of the solvent when in contact with blood. Polyvinyl acetate dissolved in dimethylsulfoxide is one such agent. Alternatively, vasoocclusive coils may be injected into the infusion catheter and delivered to a target site to occlude the blood flow at that site.

The following Examples are intended to illustrate the invention but not to limit it in any manner.

EXAMPLES

Example 1—Comparison of Burst Pressures

Prior art catheters, in particular the "ZEPHYR" catheter first marketed in 1991 were tested for burst pressure as were the inventive catheters. Pressure was applied by injecting liquid with pressures in the range of 0 to burst in 25–30 psi increments into the proximal end fitting of the catheter. The prior art catheter burst at the distal end when approximately 141 psi of pressure was applied. This value was a mean value for the catheters tested and therefore, statistically, 99.73% (3 sigma) of the values for burst pressure for the prior art catheters lie between about 97 and 185 psi. The catheters of the present invention burst at the distal end when a mean value of 207 psi of pressure was applied. 99.73% (3 sigma) of the values for burst pressure for the inventive catheters, therefore, lie between about 195 and 220 psi. The inventive catheters, therefore proved to be stronger than the prior art catheters.

Example 2—Testing of Distal End Flexibility

Figure 5:
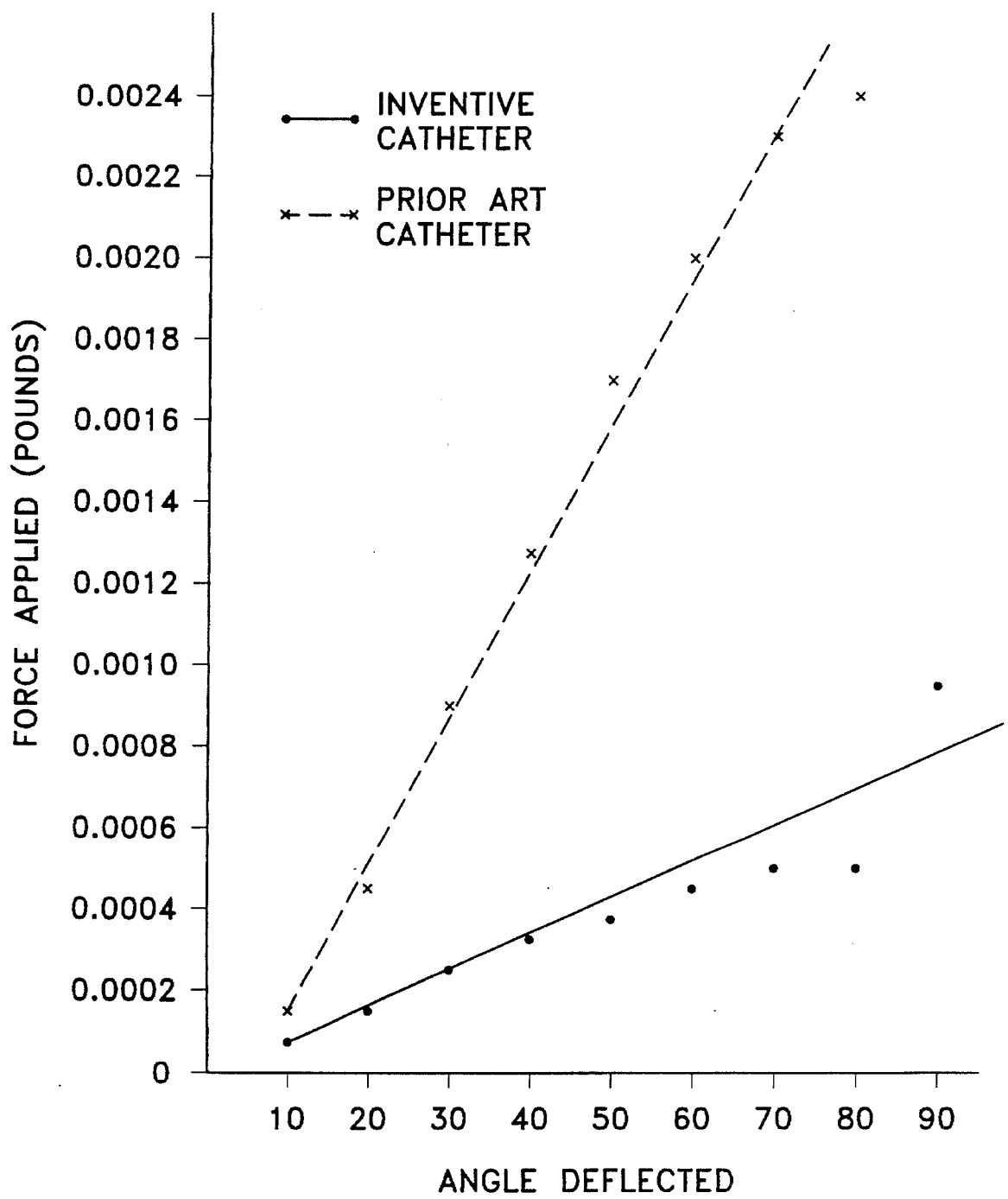
FIG. 5 is a graph showing the pounds of force corresponding to the angle that the distal segment material of the inventive catheter is deflected as compared to the distal segment material of a prior art catheter.

The flexibilities of the distal ends of the prior art "ZEPHYR" catheter and the inventive catheters were compared using a Tinius Olsen bending stiffness tester. The results are graphically described in FIG. 5.

10 centimeter portions of the distal segments of each catheter were placed on the steel plate of the Olsen stiffness tester. The material was deflected to different positions and the corresponding pounds of force recorded. When the inventive catheter was deflected 10°, the stiffness tester showed a force of $7 \times 10^{-5}$ pounds, when it was deflected 50° the force was $3.8 \times 10^{-4}$ pounds, and when the deflection was 80°, the force was $4.9 \times 10^{-4}$ pounds. The prior art catheter was deflected 10° and the stiffness tester showed a force of $7.5 \times 10^{-3}$ pounds, when it was deflected 50° the force was $8.5 \times 10^{-2}$ pounds, and when the deflection was 80°, the force was $1.23 \times 10^{-1}$ pounds. The inventive catheter, therefore, proved to be much more flexible than the prior art catheter. Upon calculation of the slope of the lines shown in FIG. 5, for the inventive catheter, a 1° deflection corresponds to $10^{-5}$ pounds of force, and for a prior art catheter, a 0.3° deflection corresponds to $10^{-5}$ pounds of force.

While preferred embodiments of the invention have been described herein, it will be recognized that a variety of changes and modifications can be made without departing from the invention.

We claim:

1. A catheter that can be guided by the blood flow within a vessel, said catheter comprising an elongate tubular member having proximal and distal ends, an inner lumen extending between these ends, and an outer surface; said tubular member comprising a flexible and strong distal segment having a burst pressure of at least about 195 psi and is made of a material which will show a force of about $10^4$ pounds or less when ten centimeters of the material is deflected 10° from horizontal; and said tubular member having a polymeric, lubricious coating on at least a portion of the outer surface, which coating has been covalently bonded to the catheter in-situ with irradiation.

2. The catheter of claim 1 wherein at least a portion of the inner lumen is coated with a polymeric, lubricious coating.

3. The catheter of claim 2 wherein the whole of the inner lumen is coated with a polymeric, lubricious coating.

4. The catheter of claim 1 where the whole of the exterior surface of the distal segment is coated with a polymeric, lubricious coating.

5. The catheter of claim 1 in which the coating is a polymer or oligomer comprising monomers selected from at least one of ethylene oxide; 2-vinyl pyridine; N-vinylpyrrolidone; polyethylene glycol acrylates, 2-hydroxyethylmethacrylate, glycerylmethacrylate; acrylic acid and its salts, acrylamide and acrylonitrile; acrylamidomethylpropane sulfonic acid and its salts; cellulose, cellulose derivatives such as methyl cellulose ethyl cellulose, carboxymethyl cellulose, cyanoethyl cellulose, cellulose acetate, polysaccharides including amylose, pectin, amylopectin, alginic acid, and cross-linked heparin.

6. The catheter of claim 1 in which the coating is a polymer or oligomer comprising monomers selected from mono-alkoxy polyethylene glycol mono(meth) acrylates, including mono-methoxy triethylene glycol mono (meth) acrylate, mono-methoxy tetraethylene glycol mono (meth) acrylate, polyethylene glycol mono (meth) acrylate.

7. The catheter of claim 1 wherein the burst pressure of the distal segment is between about 195 and 220 psi.

8. The catheter of claim 1 wherein the distal section is made of a material that further will show an additional force of about $10^{-5}$ pounds or less for each 1° of deflection of the material from horizontal.

9. The catheter of claim 1 additionally comprising a proximal segment which proximal segment is made of a polymeric material selected from the group consisting of nylon, polyvinyl chloride, polyethylene terephthalate or other polyester elastomer or of a polymer outer core with a metallic mesh inner core.

10. The catheter of claim 1 wherein the distal segment is made of a polymeric material selected from the group consisting of polyurethane, a block copolymer of polyamide, polyvinyl chloride, silicone and blends thereof.

11. The catheter of claim 1 wherein the polymeric material of the distal segment is doped with a metallic material selected from the group consisting of barium sulfate, bismuth trioxide, bismuth subcarbonate, tungsten, and tantalum.

12. The catheter of claim 1 additionally comprising a transition section located proximally of said distal section and which transition is made of a polymeric material selected from the group consisting of polyurethane, a block copolymer of polyamide, polyvinyl chloride, and silicone.

13. The catheter of claim 12 wherein the polymeric material of the transition section is doped with a metallic material selected from the group consisting of barium sulfate, bismuth trioxide, bismuth subcarbonate, tungsten, and tantalum.

14. The catheter of claim 1 wherein the distal segment is in an S-shaped configuration.

15. The catheter of claim 1 additionally comprising a guidewire located within the inner lumen.

16. A method for accessing a target site, said method comprising:

(a) inserting a guiding catheter into the vasculature;

(b) inserting the infusion catheter of claim 1 into the guiding catheter; and (c) pushing the infusion catheter out of the guiding catheter into the vasculature such that the blood flow in the vessel directs the infusion catheter to the target site.

17. The method of claim 16 which further comprises inserting a stylet into the infusion catheter in order to insert the catheter into the guiding catheter and further removing the stylet prior to pushing the infusion catheter out of the guiding catheter and into the vasculature.

18. The method of claim 17 wherein the stylet is a teflon-coated stainless steel stylet.

19. A method for delivering a diagnostic, therapeutic or vasoocclusive agent to a target site within the vasculature, said method comprising:

(a) inserting a guiding catheter into the vasculature;

(b) inserting the infusion catheter of claim 1 into the guiding catheter;

(c) pushing the infusion catheter out of the guiding catheter into the vasculature such that the blood flow in the vasculature directs the infusion catheter to the target site; and (d) injecting the diagnostic, therapeutic or vasoocclusive agent through the catheter lumen and into the target site.

20. The method of claim 19 which further comprises inserting a stylet into the infusion catheter in order to insert the catheter into the guiding catheter and further removing the stylet prior to pushing the infusion catheter out of the guiding catheter and into the vasculature.

21. The method of claim 19 wherein the vasoocclusive agent is n-butylcyanoacrylate and the target site is an arteriovenous malformation.

22. The method of claim 19 wherein the vasoocclusive agent is polyvinylacetate dissolved in dimethylsulfoxide and the target site is an arteriovenous malformation.

23. The method of claim 19 wherein the vasoocclusive agent is a vasoocclusive coil.

* * * * *

UNITED STATES PATENT AND TRADEMARK OFFICE
CERTIFICATE OF CORRECTION

PATENT NO. : 5,538,512

DATED : July 23, 1996

INVENTOR(S) : Zenzen et al.

It is certified that error appears in the above-identified patent and that said Letters Patent is hereby corrected as shown below:

Title page:
In field [19]: change "Zenzon et al." to --Zenzen et al-- .

In field [76]: change "Wendy J. Zenzon" to --Wendy J. Zenzen-- .

column 5, line 2: change "that" to --than-- .

column 8, line 38: change "is filled. The" to --is filled, the-- .

In Claim 1, column 10, line 17: change "$10^4$" to --$\mathbf{10^{-4}}$-- .

Signed and Sealed this

Tenth Day of March, 1998

Attest:

BRUCE LEHMAN

Attesting Officer    Commissioner of Patents and Trademarks